(12) United States Patent
Goldsmith

(10) Patent No.: US 10,980,664 B2
(45) Date of Patent: Apr. 20, 2021

(54) SYSTEMS AND ASSEMBLIES FOR OSTOMY APPLIANCES

(71) Applicant: Bruce Goldsmith, Beverly Hills, CA (US)

(72) Inventor: Bruce Goldsmith, Beverly Hills, CA (US)

( * ) Notice: Subject to any disclaimer, the term of this patent is extended or adjusted under 35 U.S.C. 154(b) by 405 days.

(21) Appl. No.: 14/471,246

(22) Filed: Aug. 28, 2014

(65) Prior Publication Data

US 2015/0065971 A1   Mar. 5, 2015

Related U.S. Application Data

(60) Provisional application No. 61/872,423, filed on Aug. 30, 2013.

(51) Int. Cl.
| | | |
|---|---|---|
| *A61F 5/448* | (2006.01) | |
| *A61F 5/44* | (2006.01) | |
| *A61F 5/445* | (2006.01) | |
| *A61F 5/449* | (2006.01) | |

(52) U.S. Cl.
CPC ...... *A61F 5/448* (2013.01); *A61F 2005/4495* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 3,964,485 | A | * | 6/1976 | Neumeier | A61F 5/448 604/342 |
| 4,642,107 | A | * | 2/1987 | Arnone | A61F 5/448 604/342 |
| 4,850,985 | A | * | 7/1989 | Edwards | A61F 5/448 604/339 |
| 5,088,992 | A | * | 2/1992 | Edwards | A61F 5/448 604/338 |
| 5,125,917 | A | * | 6/1992 | Whealin | A61F 5/448 604/332 |

(Continued)

FOREIGN PATENT DOCUMENTS

| | | |
|---|---|---|
| AU | 2014312343 A1 | 3/2016 |
| AU | 2014312343 B2 | 7/2019 |

(Continued)

OTHER PUBLICATIONS

International Search Report and Written Opinion for PCT/US2014/053082 dated Dec. 18, 2014, 6 pages.

(Continued)

*Primary Examiner* — Guy K Townsend
(74) *Attorney, Agent, or Firm* — Nixon Peabody LLP

(57) ABSTRACT

The present subject matter relates to medical devices for ostomy applications, specifically a floating ring design for securing robust attachment between the flange surrounding a stoma on a patient's body and an ostomy bag. Existing ostomy appliance designs present significant drawbacks related to routine, high replacement cost and poor performance, the latter resulting in anxiety, grief over fear of stool leakage due to rapid, sudden and/or unexpected detachment or mechanical compromise of ostomy appliance components. This further includes discomfort due to the mechanical stresses placed on the subject's body.

15 Claims, 8 Drawing Sheets

(56) References Cited

U.S. PATENT DOCUMENTS

| | | | | |
|---|---|---|---|---|
| 5,139,492 A * | 8/1992 | Leise, Jr. | ............... | A61F 5/448 604/332 |
| 5,178,615 A * | 1/1993 | Steer | ............... | A61F 5/448 604/338 |
| 5,180,377 A * | 1/1993 | Holtermann | ............... | A61F 5/448 604/342 |
| 5,185,008 A * | 2/1993 | Lavender | ............... | A61F 5/448 604/338 |
| 5,195,996 A * | 3/1993 | Edwards | ............... | A61F 5/448 604/332 |
| 5,312,381 A * | 5/1994 | Brooks | ............... | A61F 5/448 604/332 |
| 5,330,454 A * | 7/1994 | Klingler | ............... | A61F 5/448 604/338 |
| 5,330,455 A * | 7/1994 | McKay | ............... | A61F 5/448 604/332 |
| 5,496,297 A * | 3/1996 | Olsen | ............... | A61F 5/448 604/339 |
| 5,549,588 A * | 8/1996 | Johnsen | ............... | A61F 5/448 604/338 |
| 5,662,628 A * | 9/1997 | Hollands | ............... | A61F 5/448 604/342 |
| 5,989,235 A * | 11/1999 | Quacquarella | ............... | A61F 5/448 604/332 |
| 6,537,261 B1 * | 3/2003 | Steer | ............... | A61F 5/448 604/342 |
| 6,679,866 B1 * | 1/2004 | Gunawan | ............... | A61F 5/448 604/332 |
| 2002/0032418 A1 * | 3/2002 | Iseke | ............... | A61F 5/448 604/338 |
| 2009/0118687 A1 * | 5/2009 | Kristensen | ............... | A61F 5/448 604/342 |
| 2010/0191203 A1 * | 7/2010 | Haraldsted | ............... | A61F 5/448 604/343 |
| 2011/0295221 A1 | 12/2011 | Brown | | |

FOREIGN PATENT DOCUMENTS

| | | |
|---|---|---|
| CA | 2920496 A1 | 3/2015 |
| CN | 105555236 A | 5/2016 |
| EP | 3038573 A1 | 7/2016 |
| HK | 1225268 A | 9/2017 |
| JP | 10-305057 A | 11/1998 |
| JP | 3115054 U | 9/2005 |
| JP | 2016529029 A | 9/2016 |
| KR | 1020160048919 A | 5/2016 |
| MX | 2016002555 A | 10/2016 |
| RU | 2016111334 A | 10/2017 |
| RU | 2692954 C2 | 6/2019 |
| WO | 2015031574 A1 | 3/2015 |

OTHER PUBLICATIONS

International Preliminary Report on Patentability for PCT/US2014/053082 dated Mar. 1, 2016, 5 pages.

Chinese Office Action for CN201480047284.8 dated Mar. 1, 2017, 14 pages.

EP 14841235.6 Extended Search Report dated Jul. 19, 2017, 7 pages.

* cited by examiner

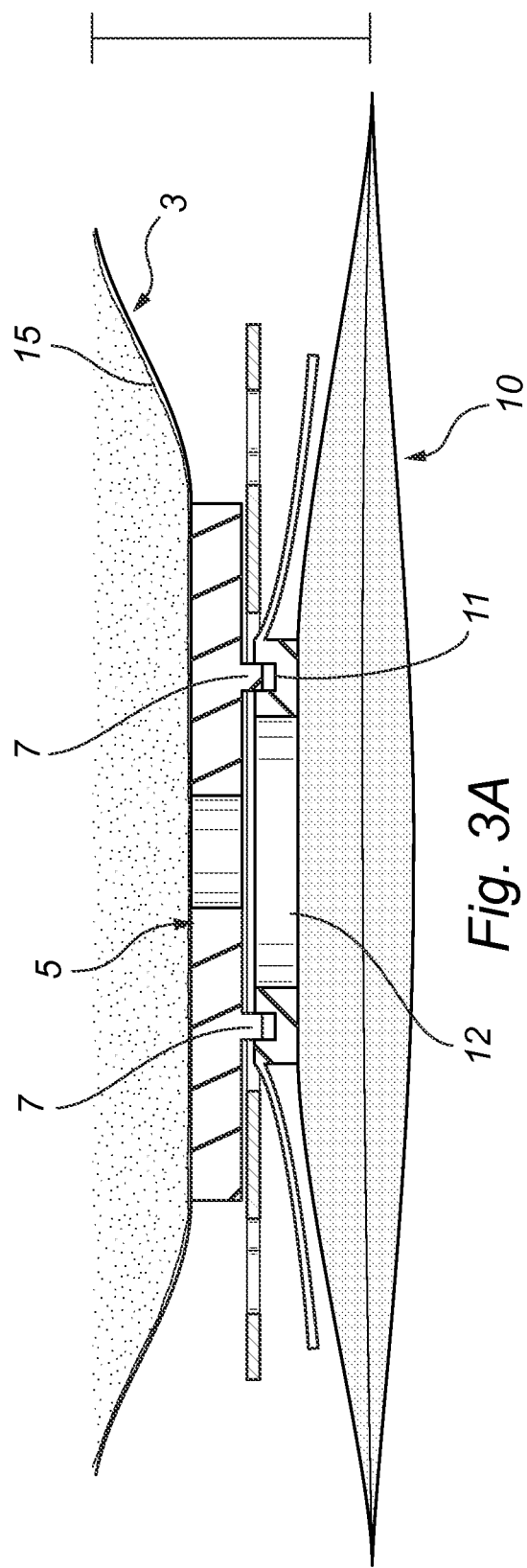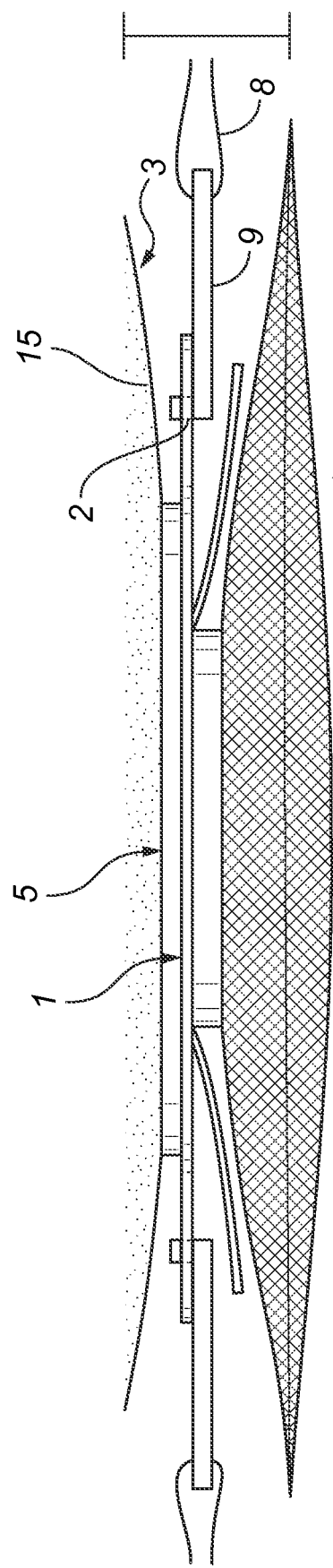
Fig. 3A
Fig. 3B

SYSTEMS AND ASSEMBLIES FOR OSTOMY APPLIANCES

FIELD OF INVENTION

The present subject matter relates to medical devices for ostomy applications, specifically a floating ring design for securing robust attachment between the flange surrounding a stoma on a patient's body and an ostomy bag.

BACKGROUND

Ostomy surgery is required when the colon, small bowel, or the urinary tract is compromised as a result of malignancy, infection, auto-immune illness, or trauma. Currently more than 100,000 ostomy surgeries are performed in the U.S. every year. Following ostomy surgery, it is common for an individual to have temporary or permanent diversion of their body's wastes to an external "pouch" known as an ostomy bag. It is estimated that perhaps one million people in the U.S. live with permanent ostomies.

Various companies produce systems to collect and dispose of the body's wastes following ostomy surgery. Common designs rely on a plastic flange, secured through adhesive to the skin, such as tissue compatible glue, for positioning and adherence around the exit stoma. This flange can be either a single-piece that is physically connected to a pouch. In single-piece designs, the unit is worn until failure, and then the complete unit is disposed of. In other designs, the flange is a two-piece system, wherein the flange is again attached to the skin, but with a separable ostomy bag that contains a circular interlocking rim that connects to a corresponding interlocking rim of the flange. In some designs, this can appear as protruding male lip and recessed female ridges on the flange and pouch ring, respectively. In two-piece designs, the pouch can be taken off and changed, allowing disposal of the pouch, while leaving the flange adhered to the skin.

These existing designs present significant drawbacks resulting in anxiety, grief, discomfort, and undesired aesthetic appearance, that lead to a compromised life style among ostomy wearers. Chief among them is fear of stool leakage due to rapid, sudden and/or unexpected detachment or mechanical compromise of ostomy appliance components. This further includes discomfort due to the mechanical stresses placed on the subject's body. Key causes include mechanical play between the ostomy bag and flange, constriction and/or friction from tensioning belts commonly used as means for securing attachment to the body. There are further drawbacks in view of the undesirable aesthetic appearance due to the outward extending ostomy bag. Existing designs attempt to address these issues by, for example, relying on the aforementioned tensioning belts to position and conceal the ostomy pouch. These designs rely on attachment points located on rings on the ostomy bag pouch, which connect to the fastening hooks of a tensioning belt. While this allows the ostomy bag to be worn closer to the body for resistance against vertical and horizontal mechanical forces acting upon the ostomy bag, such designs still suffer from significant limitations. For example, fixed attachment points on the rings or female ridges only allow inconvenient vertical orientation of the ostomy bag against the body. Further, tensioning along vertical and horizontal directions provide only limited advantages in reducing mechanical play between the flange and ostomy bag, not to mention discomfort that may result from required tightening of the tensioning belt for a secure fit In addition, the flange on the patient's body is a flexible surface, where it is difficult to ensure a durable mechanical seal between flange and ostomy bag interface, made further difficult by the flexible plastic materials pervasive in various ostomy appliances, given the inherent mechanical play between flange and ostomy bag in various existing designs.

The present invention relates to a "floating ring" for improving the attachment of an ostomy bag to the body an ostomy patient. A floating ring, made of a rigid material of a particular thickness, is positioned between a flange side ring, and a pouch side ring. An important aspect of the design is to ensure substantially even pressure of the surface of the flange, thereby limiting mechanical play and reducing clearance ordinarily present in the flange-ostomy bag interface. Placement of the floating ring in this position also allows incorporation of attachment points on the floating ring, as opposed to the female ridges of the ostomy bag. By re-positioning the attachment points to the floating ring, an ostomy bag is freely rotatable, and no longer restricted to the specific orientations as is conventionally required for attachment to the tensioning belt. Together, these improved designs provides advantages in extending the wear ability, comfort, protection, aesthetic appearance and length of time an ostomy system can be worn before leaking, failing, and needing replacement.

SUMMARY OF INVENTION

Described herein is a floating ring adapted for use with an ostomy appliance, the ostomy appliance including a flange including a flange ring, and an ostomy bag includes a pouch ring, wherein the floating ring is adapted for positioning between an annular surface of the flange ring and the annular surface of the pouch ring, wherein the flange ring and pouch ring each include a means for attachment to each other. In other embodiments, the ostomy appliance further includes a tensioning belt, the tensioning belt and the floating ring each include corresponding means for attachment to each other. In other embodiments, the flange ring includes means for attaching an ostomy bag. In other embodiments, the pouch ring includes means for attaching a flange. In other embodiments, the floating ring includes a thickness T, wherein the T is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8. 1.9, or 2.0 mm or more. In other embodiments, the floating ring includes a thickness T, wherein the T is about 0.7 to about 1.0 mm. In other embodiments, the floating ring includes an inner diameter, D, of about 0.5, 1.0, 2.0, 3.0, 4.0, 5.0, 6.0, 7.0, 8.0, 9.0, 10.0 cm or less. In other embodiments, the floating ring includes a rigid material. In other embodiments, the rigid material includes steel.

Also described herein is an ostomy appliance, including a flange including a flange ring, an ostomy bag including a pouch ring, and a floating ring, wherein the floating ring is adapted for positioning between an annular surface of the flange ring and the annular surface of the pouch ring, wherein the flange ring and pouch ring each comprise a means for attachment to each other. Further described is a method of using the ostomy appliance, including positioning the floating ring in between the flange ring and the pouch ring, aligning a stoma aperture of the flange ring, an egress aperture of the pouch ring, and the origin of the floating ring, and attaching the means of attachment between the flange ring and pouch ring. In other embodiments, the flange is attached to the body of a subject prior to positioning the floating ring in between the flange ring and the pouch ring. In other embodiments, the method includes attaching a tensioning belt to the floating ring. In other embodiments, the floating ring includes a rigid material of thickness T, wherein the T is about 0.7 to about 0.9 mm, and an inner diameter, D, of 0.5, 1.0, 2.0, 3.0, 4.0, 5.0, 6.0, 7.0, 8.0, 9.0, 10.0 cm or less. In other embodiments, the floating ring includes steel.

BRIEF DESCRIPTION OF FIGURES

Exemplary embodiments are illustrated in referenced figures. It is intended that the embodiments and figures disclosed herein are to be considered illustrative rather than restrictive.

DETAILED DESCRIPTION OF THE INVENTION

Figure 1:
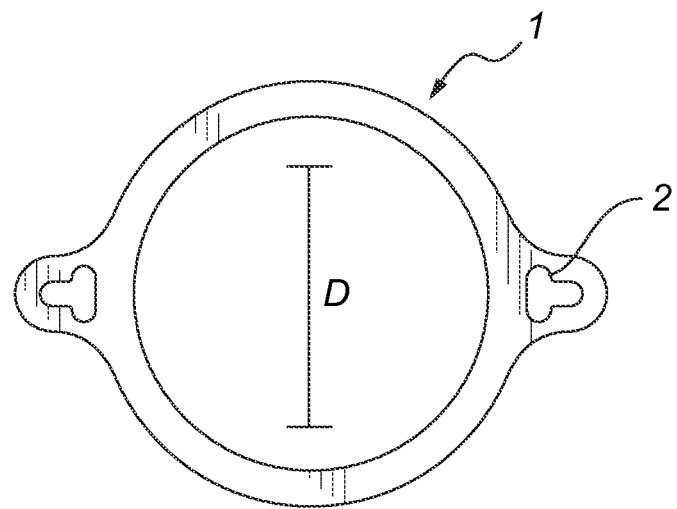
FIG. 1 Representation of floating ring. Front view of the floating ring design. In this exemplary embodiment, the floating ring 1 contains a means of attachment for connecting a tensioning belt, depicted here as grommets 2.

All references cited herein are incorporated by reference in their entirety as though fully set forth. Unless defined otherwise, technical terms used herein have the same meaning as commonly understood by one of ordinary skill in the art to which the subject matter belongs. One skilled in the art will recognize many methods and materials similar or equivalent to those described herein, which could be used in the practice of the present subject matter. Indeed, the present subject matter is in no way limited to the methods and materials described.

As described, the "floating ring" design provides improve attachment of an ostomy bag to the body of an ostomy patient. As positioned between the flange ring and the pouch ring, the use of a rigid material allows for even pressure of the surface of the flange and pouch, unlike the flexible plastic components common in ostomy appliances. The reduction in separation distance between the two flange and ostomy bag components and limits mechanical play ordinarily present in the flange-ostomy bag interface. Placement of the floating ring in this position also allows incorporation of attachment points on the floating ring, as opposed to the female ridges of the ostomy bag, thereby allowing the bag to be rotated and worn in orientations (e.g., horizontal) not possible with existing designs. Further, the use of a separable ring allows re-use of the ring with a variety of ostomy appliances, providing benefits across multiple devices, but without requiring increased manufacturing cost due to incorporation of the ring in components of various ostomy appliances. An improved device would provide immense benefits for enhanced physical and emotional security from the ever-present fears of unpredictable, embarrassing, appliance failure leakage due to rapid, sudden and/or unexpected detachment or mechanical compromise of existing ostomy appliances. An additional benefit would be a significant reduction in cost to the ordinary ostomy appliance user. It is estimated that one may spend $3,000-$3,500 on average per year for ostomy appliance components, as requiring replacement of the ostomy appliance in its entirety every three days.

By contrast, an improved device allowing for 5-7 days of continuous wear would result in a minimum cost reduction of 50%. Estimating for the 1.2 million patients who rely on such devices, this cost savings would be highly significant for the public and healthy care sectors.

The ostomy ring maintains even pressure around the entire perimeter of the flange seal and provides at least the following advantages, in various embodiments: (1) it may be self-aligning; (2) it can be rotated at any angle and does not need to be locked into one position, allowing the pouch to be set at any angle from vertical to horizontal; (3) its seal may extend the durability of the flange and system from 50% to 100% allowing for up to seven days of total reliability; (4) it may provide enhanced physical and emotional security from the ever-present fears of unpredictable, embarrassing, appliance failure leakage; (5) it may offer improved skin health due to no leakage; (6) it may offer improved comfort due to a pouch that can be rotated into a comfortable angle without having to be locked in only a vertical position; (7) it may have an improved appearance with the use of the a belt concealing the ostomy appliance; (8) it may have a lower cost than conventional devices; (9) it may provide support to the anatomy surrounding the stoma, potentially preventing parastomal hernias; (10) the cost of the stainless steel ring is a one-time purchase for the user and may last indefinitely; and (11) production costs may be minimal.

Figure 2A:
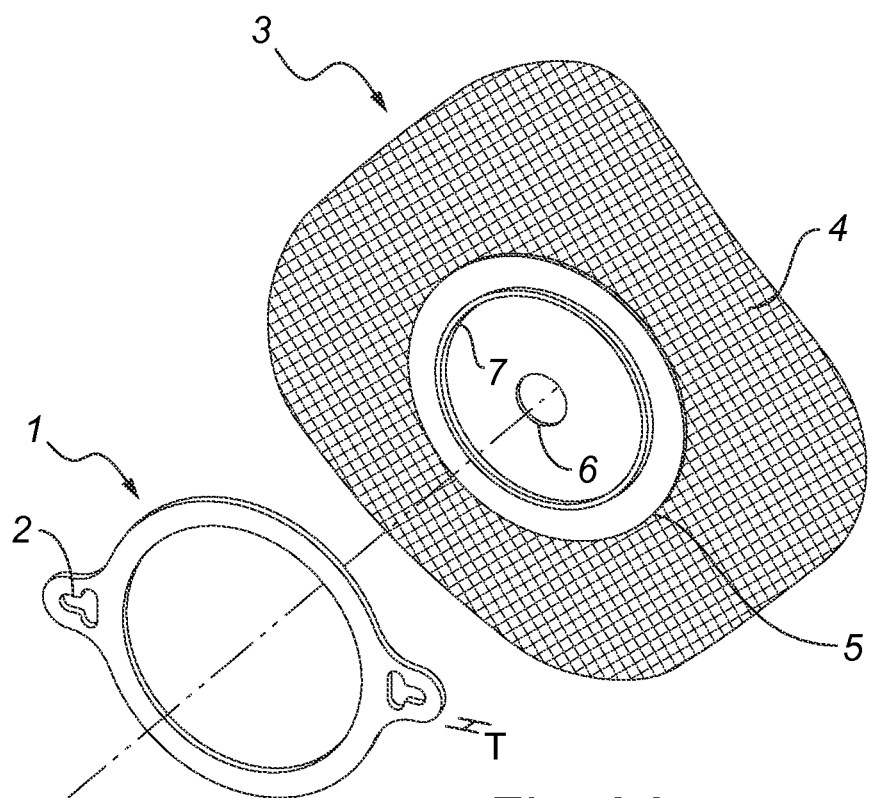
FIG. 2 Components of the ostomy bag assembly including floating ring, flange, tensioning belt, and ostomy bag. (A) Assembly of floating ring 1 and flange 3. As depicted, the floating ring 1 rests in substantially coplanar fashion against the surface of the flange 3—the component placed on the patient's body. The flange 3 contains an attachment surface 4, and annular surface flange ring 5 surrounding the stoma aperture 6. As depicted, the annular surface of the floating ring 1 is eventually positioned so as to be substantially coplanar with the annular surface of the flange ring 5. When assembled, the floating ring 1 overlaps with the flange ring 5. In certain embodiments, inner diameter of the floating ring 1 exceeds the diameter of male lip 7 presented on the surface of the annular surface flange ring 5, so as to allow them to remain exposed for coupling to an ostomy bag 10. (B) Assembly of floating ring 1 with flange 3 and tensioning belt 8. The floating ring 1 contains means for attachment, depicted here as grommets 2 that allow corresponding means for attachment, depicted as fastening hooks 9, on a tensioning belt 8 to fasten the ostomy appliance to the body. (C) Flange 3 and ostomy bag 10 contain corresponding interlocking regions, depicted here as a protruding male lip 7 on an annular surface of the flange 3 surrounding the stoma aperture 6, and complementary female recessed ridges 11 on an annular surface of the pouch ring 12 surrounding an egress aperture 14. Attachment points on the annular surface of the pouch ring 12 as representative of the existing designs in the art. This is in contrast to embodiments of the claimed inventions, wherein means for attachment points positioned on the ring itself (D) The assembly of FIG. 2B is depicted as positioned with assembly to the ostomy bag 10. As shown, the floating ring, resting substantially in substantially coplanar fashion against the surface of the flange 3, is then further assembled as coplanar with the annular surface of the pouch ring 12. The male lip 7 on the annular surface of the flange ring 5 surrounding the stoma aperture 6 interlocks with the female recessed ridges 11 on an annular surface of the pouch ring 12 surrounding an egress aperture 14. (E) As further depicted, the floating ring 1 is positioned between the flange 3 and the ostomy bag 10.

More specifically, an embodiment of an exemplary floating ring 1 in accordance with embodiments of the invention is shown in FIG. 1 in a front-facing view. The ring is an annular surface of variable diameter, which may optionally contain means for attachment. In certain embodiments, this includes means for attachment, such as the exemplary grommets 2 depicted in FIG. 1. In different embodiments, the floating ring 1 is an annular surface of variable diameter, D, that has a thickness, T, as shown in FIG. 2A in ¾ perspective, and a compatible flange 3 is shown in FIG. 2A. The flange 3 contains both an attachment surface 4 for contacting with a patient's skin, and the annular surface of a flange ring 5, wherein the attachment surface 4 surrounds the annular surface of the flange ring 5, and the flange ring 5 is positioned so as to encompass the stoma aperture 6. In some instances, the stoma aperture 6 is positioned approximately at the origin of the annular surface. The flange ring 5 can further contain a protruding (i.e., outward extending) male lip 7 on the surface of a compatible annular surface on the flange ring 5. In certain embodiments, the inner diameter of the floating ring 1 can be adapted so as to exceed the diameter of male lip 7 on the surface of the annular surface flange ring 5, thereby allowing the producing male lip 7 to remain exposed for later coupling to an ostomy bag 10. It is appreciated that inside diameter, D, and a corresponding flange may be separated by a distance, S, wherein the distance, S, is large enough to provide clearance when passaging of an ostomy bag through the ring, and/or of distance S is small enough to secure, flatten skin and/or otherwise be close enough to a stoma and/or skin surrounding a stoma.

Figure 2B:
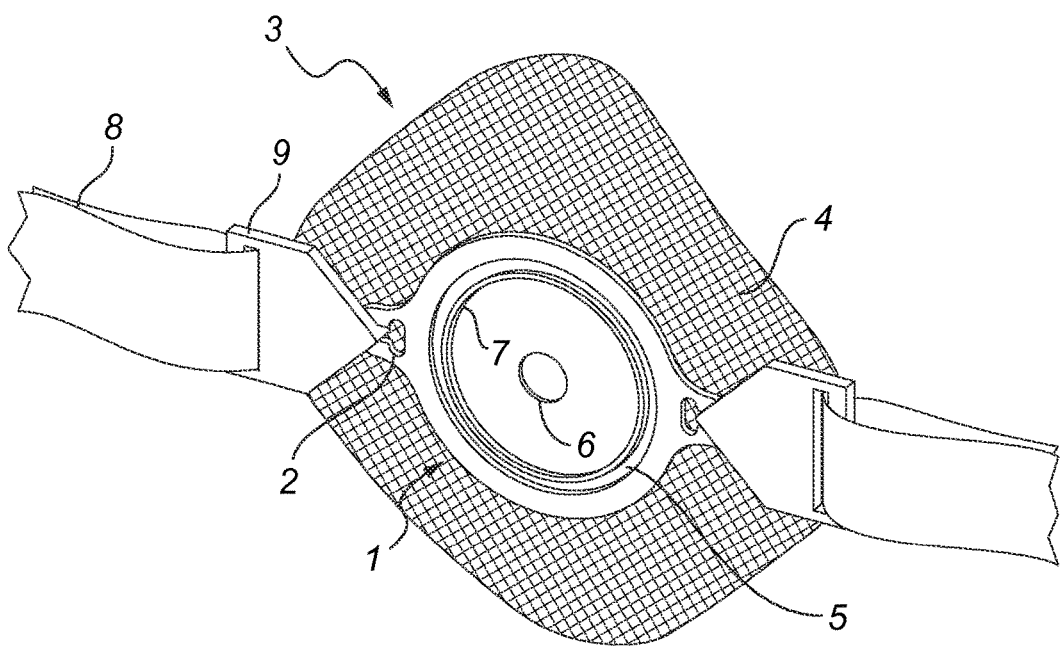

In accordance with certain embodiments, an assembly shown in FIG. 2B, includes an annular surface of the floating ring 1 positioned so as to be substantially coplanar with the annular surface of the flange ring 5. In some embodiments, the floating ring 1 and flange 3 both can be positioned so that their origins are all approximately located at the position of the stoma aperture 6. For embodiments shown in FIG. 2B, an assembly of the floating ring 1, flange 3, and tensioning belt 8 is depicted. As shown, the overlapping coplanar surface of the floating ring 1 and annular surface of the flange ring 5 nevertheless allow for the male lip 7 to be exposed. The floating ring 1 contains means for attachment, depicted here as grommets 2 for corresponding means for attachment on a tensioning belt 8 to fasten, said means for attachment on the tensioning belt 8 depicted here as fastening hooks 9.

Figure 2C:
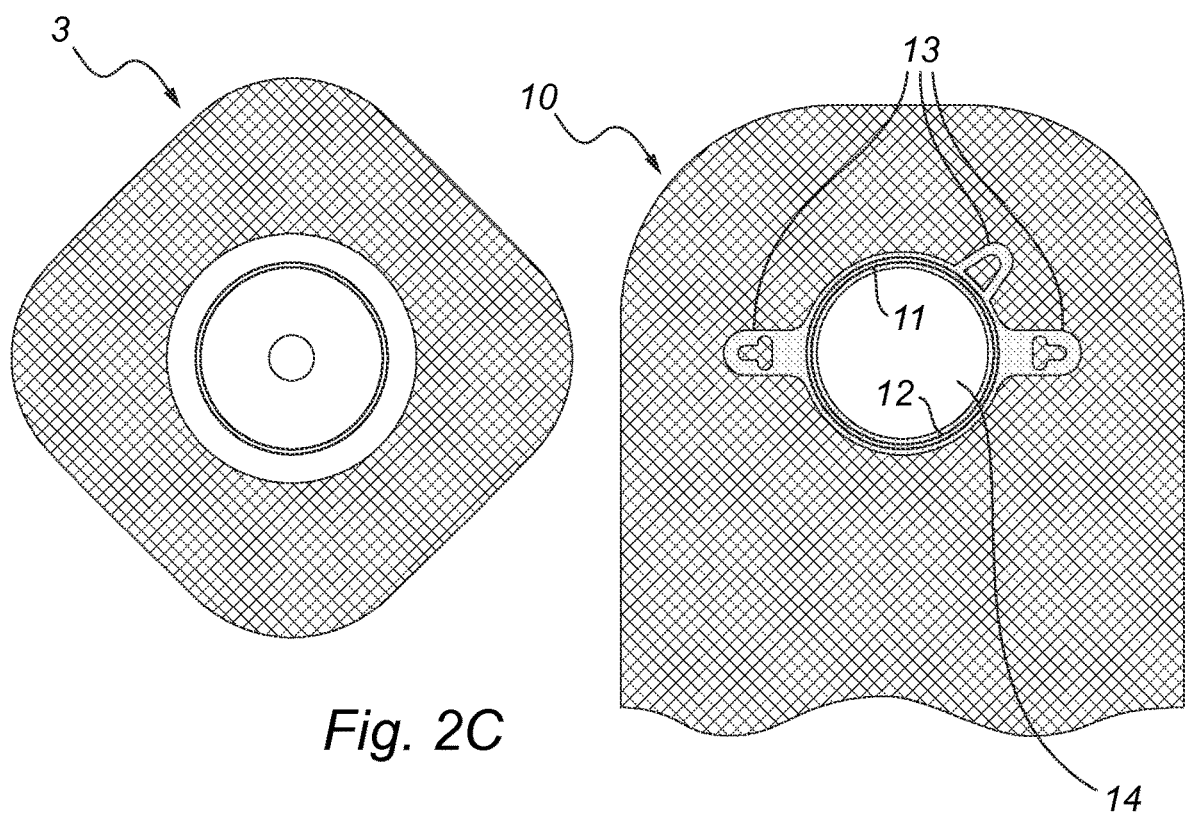

As related to different embodiments, the additional components for use with the floating ring 1 include the described flange 3, and a compatible ostomy bag 10, each shown in front facing view in FIG. 2C. The flange 3 and ostomy bag 10 contain corresponding interlocking regions, depicted here as a protruding male lip 7 on an annular surface of the flange ring 5 surrounding the stoma aperture 6, and complementary female recessed ridges 11 on an annular surface of the pouch ring 12 surrounding an egress aperture 14 on the pouch. The fixed attachment points on the annular surface of the pouch ring 12 are representative of the existing designs in the art.

Figure 2D:
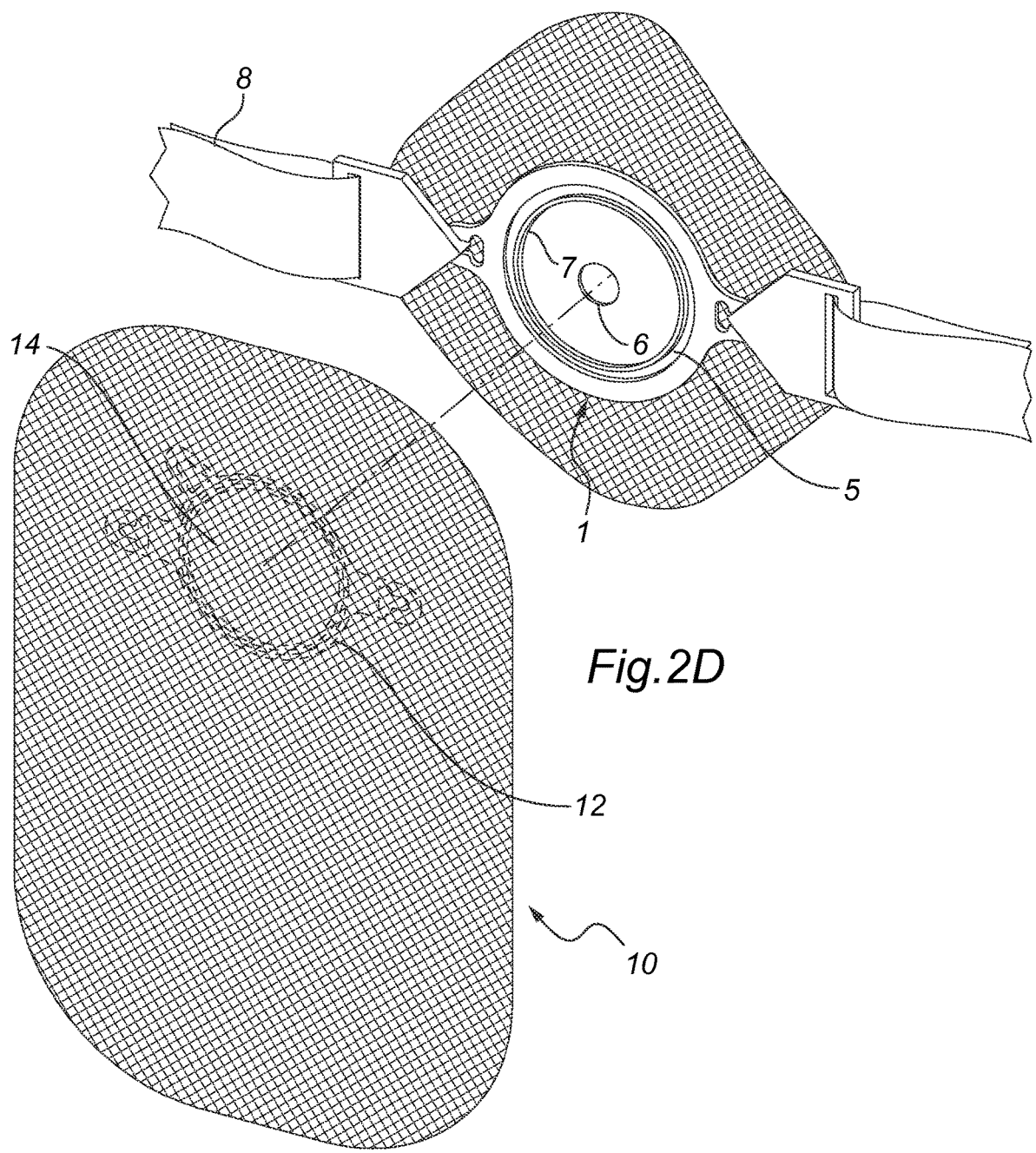
Figure 2E:
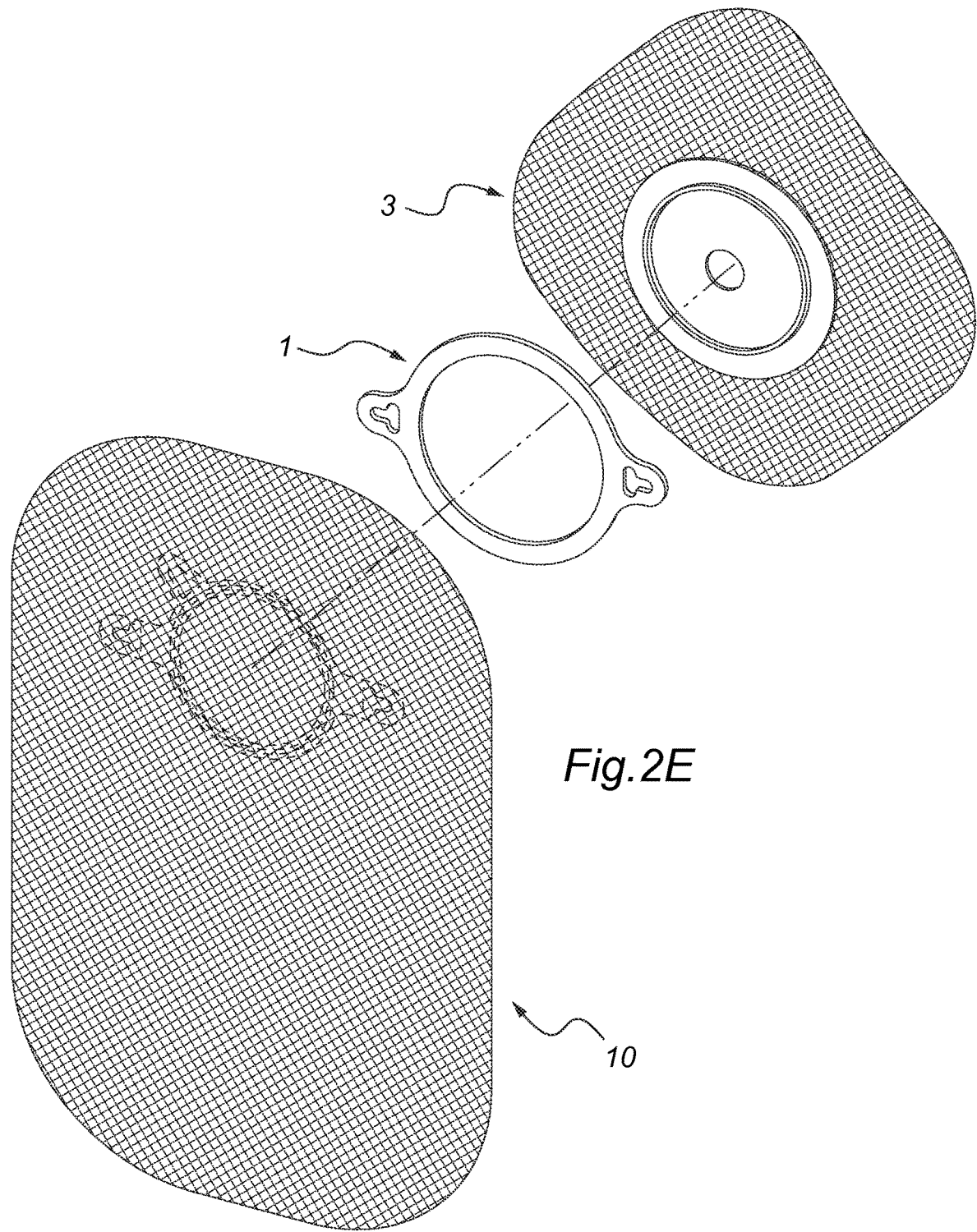

Further assembly of the various described components in certain embodiments is shown in FIG. 2D, wherein the partial assembly of FIG. 2B is positioned for further assembly to the ostomy bag 10. As shown, the floating ring 1 rests in substantially coplanar fashion against the annular surface of the flange ring 5. In the depicted embodiments, the respective origins surround the stoma aperture 6 and are then further assembled in substantially coplanar fashion with the annular surface of the pouch ring 12. Certain embodiments provide for the origins of floating ring 1, annular surfaces of the pouch ring 12, and flange ring 5 to be approximately at the same point. This includes, for example, the stoma aperture 6 on the flange 3 and/or egress aperture 14 on the pouch. In accordance with different embodiments, the flange 3 and ostomy bag 10 attached via the protruding male lip 7 on the annular surface of the flange ring 5 interlock with the female recessed ridges 11 on an annular surface of the pouch ring 12. As described, certain embodiments of the floating ring 1 contain means for attachment, depicted here as grommets 2 for corresponding means for attachment on a tensioning belt 8 to fasten, the means on the tensioning belt 8 depicted here as fastening hooks 9. The In accordance with certain embodiments, an assembly is shown in FIG. 2E, this time in exploded ¾ perspective to emphasize final positioning of the ring in between the flange ring 5 of the flange 3 and the pouch ring 12 of the ostomy bag 10.

As readily appreciated by one of ordinary skill, the floating ring is compatible with a variety of existing systems. As the ring is not incorporated into the flange or the ostomy bag, it is freely rotatable about the axis extending outward from the stoma. This self-aligning aspect means that the floating ring is not locked into any one position, unlike existing designs. A further advantage can be seen in that the ring diameter D can be great enough so that it can be removed or attached without removing the ostomy bag. For example, an ostomy bag attached to a flange can be gently compressed/folded, and laterally moved through the greater inner diameter of the ring.

Figure 3C:
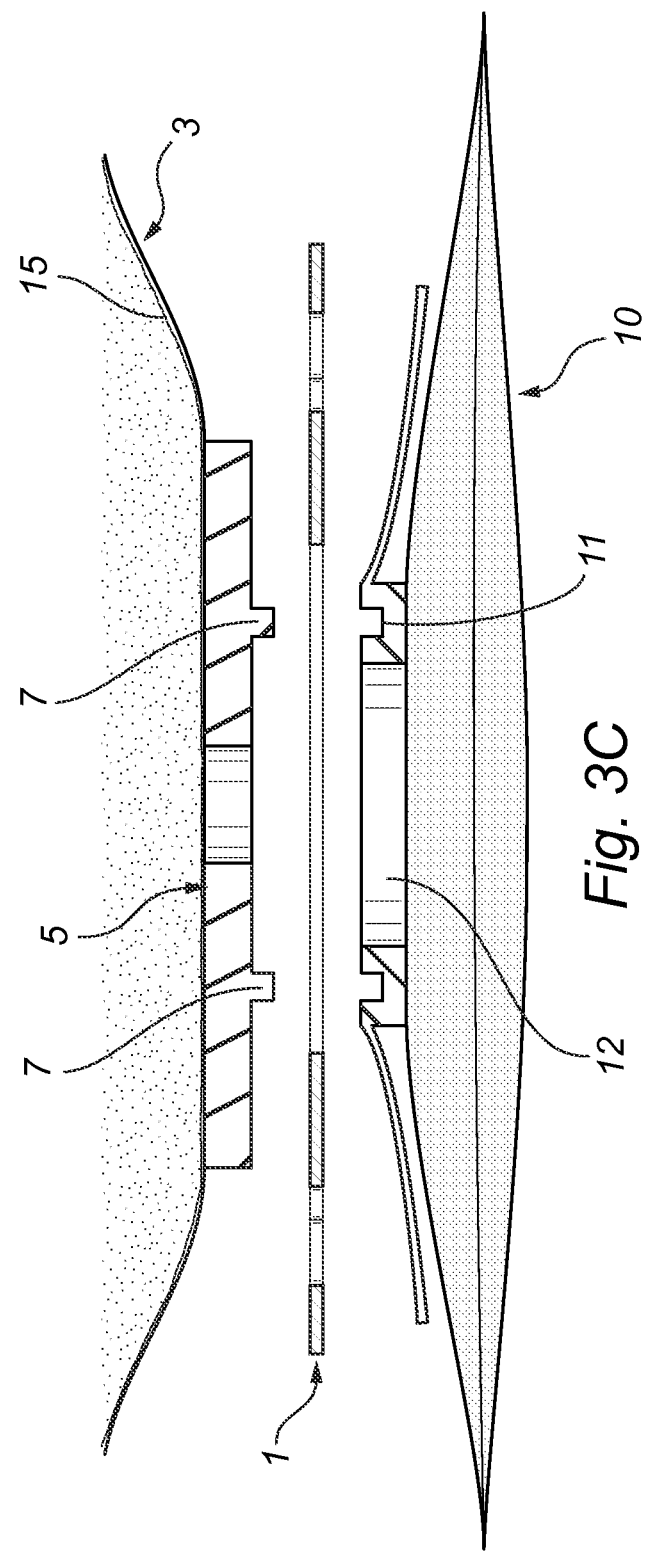
FIG. 3 Side view of assembly. (A) This exemplary depiction of existing designs (prior art) shows the interface of flange 3 and ostomy bag 10. Here, the annular surface flange ring 5 is coupled to the female recessed ridges 11 on an annular surface of the pouch ring 12 via male lip 7. The skin surface 15 does not rest completely flat against the assembly. (B) The improved design of the present invention positions the floating ring 1 in between the flange ring 5 and pouch ring 12, allowing for more even pressure distribution across the seal, reduction in mechanical play and undesired spacing between flange 3 and ostomy bag 10. This includes flattening of the skin surface 15 for a more durable seal. As further depicted, the floating ring 1 contains means for attachment, shown here as grommets 2, wherein corresponding means for attachment from tensioning belt 8 are connected, shown here as fastening hooks 9. (C) The existing design depicted in FIG. 3(A) is shown here in an exploded view.

A cross-sectional view of the complete assembly is shown in FIG. 3. An exemplary depiction of existing designs shows the interface of flange 3 and ostomy bag 10 in FIG. 3A. Here, the annular surface flange ring 5 is coupled to the female recessed ridges 11 on an annular surface of the pouch ring 12. A significant amount of mechanical play exists within such existing designs between the flange ring 5 and the pouch ring 12, as can be measured between the distance of the flange ring 5 and the pouch ring 12. This is due, in part, to the relatively soft and malleable plastic surfaces used for flange 3 and pouch rings 12 in many existing designs, which poorly resist mechanical deformation as a result of stress. By contrast, the improved design is shown in FIG. 3B, wherein the floating ring 1 is again positioned between the flange 3 and ostomy bag 10. The improved design results in decreased mechanical play and reduction in undesired spacing that results from the use of a rigid material of even pressure on the surfaces of the flange ring 5 and pouch rings 12. The floating ring 1 incorporates use of a material with high resistance to mechanical deformation as a result of stress (i.e., rigid materials).

Another benefit of the present system includes compatibility with a variety of existing systems. A great number of patients experience a recessed or retracted stoma, wherein the stoma does not fully extend outward from the body. When not a stoma is not fully exposed, outward effluent originating from the stoma is not able to efficiently drain in to the ostomy bag. In some instances, effluent can leak onto the skin or flange, causing discomfort and pain. Some designs have deployed a convex shape in order to apply pressure to the skin surrounding the stoma, for fuller extension from the body. The floating ring is also compatible with these designs.

Figure 4A:
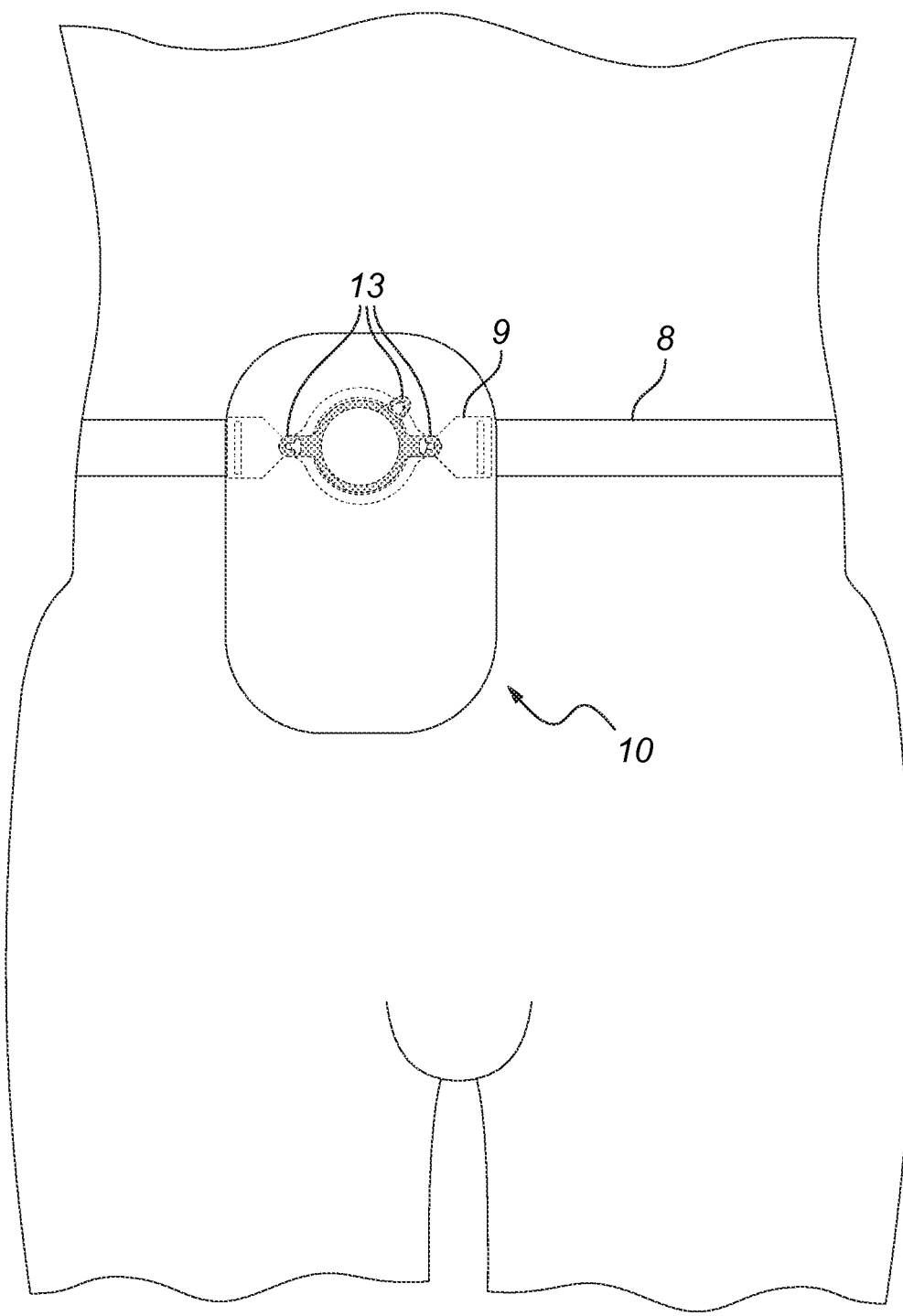
FIG. 4 Assembly worn by user (A) Exemplary depiction of existing design shows the fixed attachment ears 13 commonly located on the pouch rings 12. Positioning of the attachment ears 13 at the 3 and 9 o'clock positions allows lateral tensioning to resist horizontal forces. Alternative or additional attachment ears 13 can be positioned at the 2 o'clock positioning for wearing the tensioning belt 8 across the shoulder for lateral and longitudinal tensioning to resist both horizontal and vertical forces. Ultimately, positioning of the ears on the pouch ring 12 in this manner of existing designs allows it only to be worn in the vertical position. (B) Improved design positions attachment points on the floating ring. In this aspect, the ring can be rotated freely, allowing the tensioning belt 8 or the bag to be positioned as desired by the user. In the exemplary depiction, the ostomy bag 10 is rotated sideways to allow for horizontal wearing. Attachment points on the pouch in existing designs are depicted for comparison.
Figure 4B:
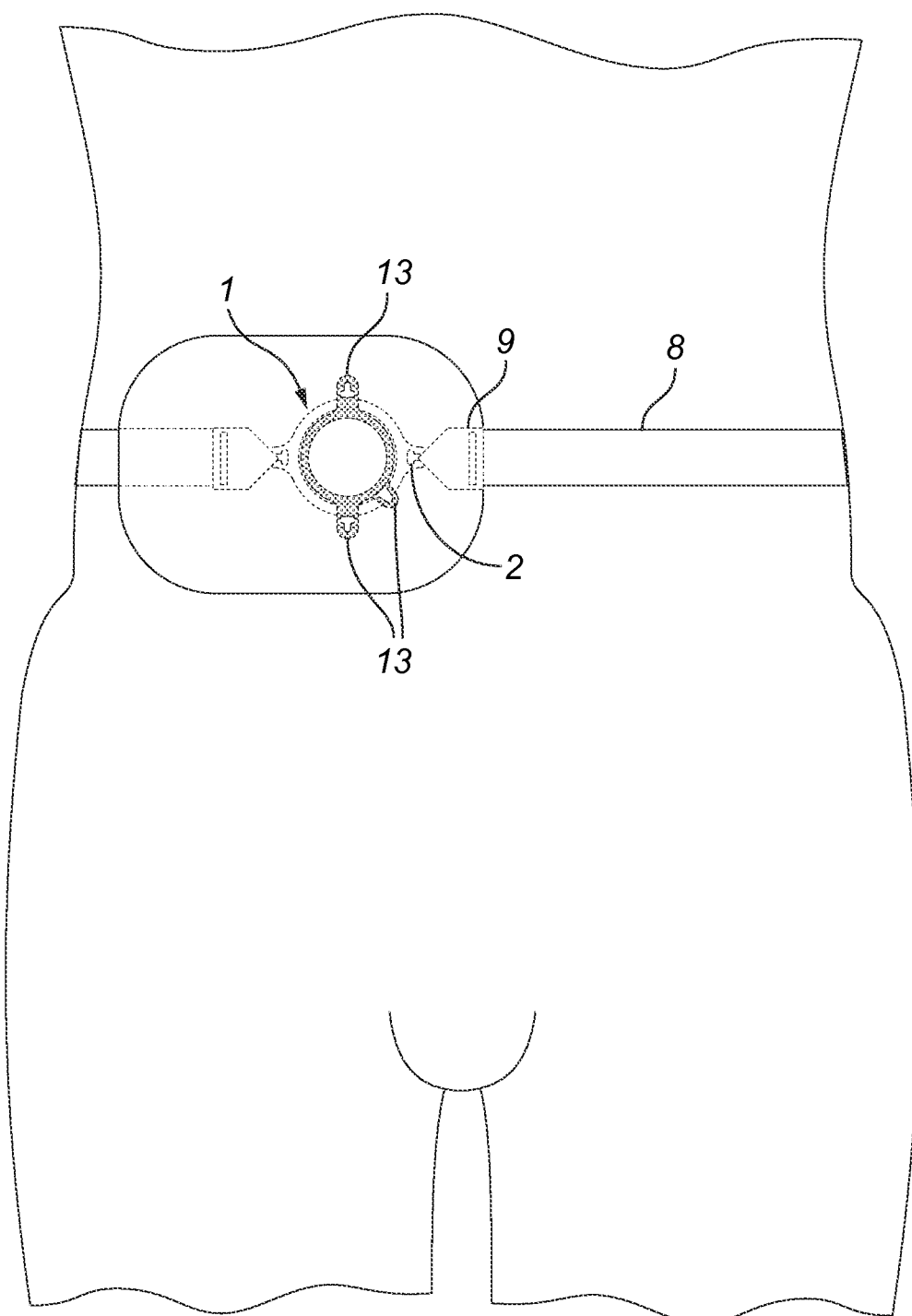

In other embodiments, an exemplary depiction of an existing ostomy bag 10 design is shown in FIG. 4A, when worn across the body. As described, the attachment points in existing designs are typically located on the pouch ring 12. The exemplary depiction of existing designs in FIG. 4A shows the attachment ears 13 located on the pouch ring 12, with positioning of the attachment ears 13 at the 3 and 9 o'clock positions being common. With these existing designs, positioning in this manner allows lateral tensioning to resist horizontal forces, and in some other existing designs, alternative or additional attachment ears 13 can be positioned at the 2 o'clock positioning for wearing the belt across the shoulder to provide longitudinal tensioning to resist vertical forces. A significant drawback of these designs is limited opportunity to adjust the bag position for comfort or improved aesthetic appearance, such as limited vertical position depicted in FIG. 4A. By contrast, improved design positions attachment points on the floating ring 1 allow for much more flexible positioning of the ostomy bag 10, such as the horizontal orientation shown in FIG. 4B. In this aspect, as the ring is not fixed to either the flange 3 or ostomy bag 10, the ring and its means for attachment to a tensioning belt 8 can be rotated freely about the axis extending outward from the origin of the ring. This self-aligning aspect means that the floating ring is not locked into any one position, and a superior advantage over existing designs. As shown, the bag can rotated sideways to allow for horizontal wearing for improved comfort and aesthetic appearance. Alternative placements of the floating ring 1 can be alongside the ostomy bag 10 side of the assembly, wherein the floating ring 1 sits between the ostomy bag 10 and attachments ears 13. This can be achieved by bending the flexible attachment ears 13 inward, with the floating ring 1 laterally positioned over the bent attachment ears 13, and released once the floating ring 1 has been situated. Described herein is a floating ring adapted for use with an ostomy appliance. In certain embodiments, the ostomy appliance is a single unit. In other embodiments, the ostomy appliance is a two-piece unit. In various embodiments, the ostomy appliance includes a flange and an ostomy bag. In other embodiments, the ostomy appliance further includes a tensioning belt. In various embodiments, the flange includes an attachment surface connected to an annular surface that is a flange ring, with the origin of the flange ring surrounding a stoma aperture. In other embodiments, the flange ring contains means for attaching an ostomy bag. This can include, as an example, a protruding male lip adapted for connection with corresponding recessed female ridges positioned on an ostomy bag. In other embodiments, this can includes hook and loop designs, clips, adhesives or screws. In various embodiments, the ostomy bag includes a bag, and an annular surface of the pouch ring surrounding an egress aperture on the ostomy bag. In various embodiments, the ostomy bag includes a pouch ring, with the origin of the pouch ring surrounding an egress aperture. In other embodiments, the pouch ring contains means for attaching to a flange. This can include, as an example, female recessed ridges adapted for interlocking connection with a corresponding protruding male lip positioned on a flange. In other embodiments, this can includes hook and loop designs, clips, adhesives or screws.

In other embodiments, the floating ring possesses a thickness T, wherein the T is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8. 1.9, or 2.0 mm or more. In other embodiments, T is 3.0, 4.0, 5.0, 6.0, 7.0, 8.0, 9.0, 10.0, 11.0, 12.0, 13.0, 14.0, 15.0, 16.0, 17.0, 18.0, 19.0, 20.0 mm or more. In some embodiments, T, is about 0.7 to about 1.0 mm. In some embodiments, T, is about 0.9 mm. In other embodiments, the floating ring possess an inner diameter, D, of 0.5, 1.0, 2.0, 3.0, 4.0, 5.0, 6.0, 7.0, 8.0, 9.0, 10.0, 11.0, 12.0, 13.0, 14.0, 15.0 cm or more. In other embodiments, the floating ring possess an inner diameter, D, of 0.5, 1.0, 2.0, 3.0, 4.0, 5.0, 6.0, 7.0, 8.0, 9.0, 10.0 cm or less. In other embodiments, the inner diameter, D, is greater than the diameter of the flange ring that the floating ring is adapted for use with. In other embodiments, the floating ring possesses a diameter and/or circumference that is capable of surrounding the means for attaching an ostomy bag that is on the flange ring. In other embodiments, the inner diameter, D, is greater than the diameter of the pouch ring that the floating ring is adapted for use with. In other embodiments, the floating ring possesses a diameter and/or circumference that is capable of surrounding the means for attaching a flange that is on the ostomy bag. In this regard, it is appreciated that inside diameter, D, and a corresponding flange may be separated by a distance, S, wherein the distance, S, is large enough to provide clearance when passaging of an ostomy bag through the ring, and/or of distance S is small enough to secure, flatten skin and/or otherwise be close enough to a stoma and/or skin surrounding a stoma. This allows, for example, an alternative installation wherein one can by bending the flexible attachment ears 13 inward, with the floating ring 1 laterally positioned over the bent attachment ears 13, and released once the floating ring 1 has been situated. In different embodiments, the floating ring is positioned between the flange and the ostomy bag when using with the ostomy appliance.

In other embodiments, the floating ring includes means for attachment to a tensioning belt. This can include, for example, grommets, holes, protruding geometric shapes, fasteners such as hook and loop designs, clips, adhesives or screws. In other embodiments, the tensioning belt includes corresponding means for attachments, such as fastening hooks, hook and loop designs, clips, adhesives or screws. In various embodiments, the floating ring, can contain, one, two, three, four, five, six, seven, eight, nine, ten or more point of attachment to the tensioning belt.

In various embodiments, the floating ring is can be constructed out of rigid materials that resist mechanical deformation. For example, one manner of describing rigidity of a material is a high Young's Modulus, wherein the material experiences limited mechanical deformation (strain) in response to a tensioning force (stress). In different embodiments, the rigid material possesses a Young's Modulus of at least 50, 60, 70, 80, 90, 100, 110, 120, 130, 140, 150, 160, 170, 180, 190, 200, 210, 220, 230, 240, 250 gigaPascals (GPa) or higher. For example, the Young's modulus of metals such as steel is 200 GPa. Alternatively, rigidity can be described in terms of compressive strength, or shear strength, or ductility. Rigidity can be described in terms of ultimate strength combining these features, and in different embodiments, the rigid material possess an ultimate strength of 100, 200, 300, 400, 500, 600, 700, 800, 900, 1000, 1100, 1200, 1300, 1400, 1500, 1600, or 1600 or more megaPascals (MPa). For example, the ultimate strength of steel is 400 MPa. One of ordinary skill will recognize that rigid materials will therefore include materials such as steel, titanium, aluminum, carbon fiber, among others.

In other embodiments, the ostomy bag can be worn for 1, 2, 3, 4, 5, 6, 7, 8, 9, 10, 11, 12, 13, 14 days or more. In other embodiments, the ostomy bag can be worn for 2 weeks, 3 weeks, 4 weeks or more.

Also described herein is an ostomy appliance including a flange, an ostomy bag, and a floating ring. In certain embodiments, the ostomy appliance is a single unit. In other embodiments, the ostomy appliance is a two-piece unit. In other embodiments, the ostomy appliance further includes a tensioning belt.

In other embodiments, described herein is a method of using the ostomy appliance of including positioning the floating ring in between the flange ring and the pouch ring, aligning a stoma aperture of the flange ring, an egress aperture of the pouch ring, and the origin of the floating ring, and attaching the means of attachment between the flange ring and pouch ring. In other embodiments, the flange is attached to the body of a subject prior to positioning the floating ring in between the flange ring and the pouch ring In other embodiments, the method includes attaching a tensioning belt to the floating ring. In other embodiments, the floating ring includes a rigid material of thickness T, wherein the T is about 0.7 to about 0.9 mm, an inner diameter, D, of 0.5, 1.0, 2.0, 3.0, 4.0, 5.0, 6.0, 7.0, 8.0, 9.0, 10.0 cm or less. In other embodiments, the floating ring is made of steel.

Further described herein is a method of using a floating ring adapted for use with an ostomy appliance. In various embodiments, the ostomy appliance includes a flange and an ostomy bag. In other embodiments, the ostomy appliance further includes a tensioning belt.

In various embodiments, the method begins with attaching a flange to the surface of the skin, positioning the floating ring near or on an annular surface that is a flange ring of the flange, wherein the floating ring and annular surface are substantially coplanar, connecting an ostomy bag, wherein floating ring, flange ring, and the annular surface of the pouch ring of the ostomy are all substantially coplanar.

In some embodiments, the origin of the floating ring, flange ring, and pouch ring are substantially aligned. In various embodiments, the substantial alignment is proximal to a stoma aperture and/or egress aperture. In other embodiments, the flange is pre-attached to the surface of the skin. In various embodiments, connecting an ostomy bag further includes coupling of corresponding means of attachment located on the flange ring and pouch ring. This can include, for example, interlocking the female recessed ridges adapted for connection with a corresponding protruding male lip positioned on a flange. In other embodiments, the method further includes attachment of a tensioning belt, wherein the belt worn in horizontal, vertical, or in any other orientations provided by rotation of the floating ring around the flange ring and/or pouch ring.

EXAMPLES

Results of Improved Design

A significant amount of undesired spacing can be present between the flange and ostomy bag in conventional systems, which is a source of mechanical play between the two separable components. Insertion of the floating ring and use of a tension belt in between the flange and ostomy bag essentially eliminates undesired spacing between the two components, thereby ensuring a more durable seal between the two components.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the designs, materials, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A floating ring adapted for use with an ostomy appliance, the ostomy appliance comprising:
   a flange comprising a flange ring; and
   an ostomy bag comprising a pouch ring, wherein the floating ring is adapted for positioning between an annular surface of the flange ring and the annular surface of the pouch ring, wherein the flange ring and pouch ring each comprise interlocking regions capable of directly interlocking the flange ring and the pouch ring to each other through an inner diameter of the floating ring,
   wherein the inner diameter of the floating ring, ID, is 5.0 to 9.0 cm, including the ranges of 5-6, 6-7, and 8-9 cm, and wherein the thickness, T, is 0.7 to 2 mm of an entirety of the floating ring, wherein an outer diameter of the floating ring does not extend beyond the surface area of the flange, and wherein the floating ring is entirely planar and non-concave, and wherein the floating ring is made of material with a Young's modulus of about 170 to 210 gigaPascals.

2. The floating ring of claim 1, wherein the ostomy appliance further comprises a tensioning belt, wherein the tensioning belt and the floating ring are attachable to each other.

3. The floating ring of claim 1, wherein the interlocking region of the flange ring comprises a protruding male lip that removably attaches to the interlocking region of the ostomy bag.

4. The floating ring of claim 1, wherein the interlocking region of the pouch ring comprises a female recessed ridge that removably attaches to the interlocking region of the flange.

5. The floating ring of claim 1, wherein the material comprises steel.

6. An ostomy appliance, comprising:
   a flange comprising a flange ring;
   an ostomy bag comprising a pouch ring; and
   a floating ring, wherein the floating ring is adapted for positioning between an annular surface of the flange ring and the annular surface of the pouch ring, wherein the flange ring and pouch ring each comprise interlocking regions capable of directly interlocking the flange ring and the pouch ring to each other through an inner diameter of the floating ring, wherein the inner diameter of the floating ring, ID, is 5.0 to 9.0 cm, including the ranges of 5-6, 6-7, and 8-9 cm, and wherein the thickness, T, is 0.7 to 2 mm of an entirety of the floating ring, wherein an outer diameter of the floating ring does not extend beyond the surface area of the flange, wherein the floating ring is entirely planar and non-concave, and wherein the floating ring is made of material with a Young's modulus of about 170 to 210 gigaPascals.

7. A method of using the ostomy appliance of claim 6, comprising:
   positioning the floating ring in between the flange ring and the pouch ring;
   aligning a stoma aperture of the flange ring, an egress aperture of the pouch ring, and an origin of the floating ring; and
   attaching the interlocking regions of the flange ring and pouch ring.

8. The method of claim 7, wherein the flange is attached to the body of a subject prior to positioning the floating ring in between the flange ring and the pouch ring.

9. The method of claim 7, further comprising attaching a tensioning belt to the floating ring.

10. The floating ring of claim 1, wherein the floating ring comprises steel.

11. The floating ring of claim 2, wherein the tensioning belt and the floating ring are removably attached using a grommet, a fastening hook, a hook and loop design, a clip, an adhesive, a screw, or a combination thereof.

12. The floating ring of claim 1, wherein the interlocking region of the flange ring has an outer diameter, OD1, that is less than the ID.

13. The ostomy appliance of claim 6, wherein the interlocking region of the flange ring has an outer diameter, OD1, that is less than the ID.

14. The floating ring of claim 1, wherein the outer diameter of the floating ring is no greater than an outer diameter of the annular surface of the flange ring.

15. The ostomy appliance of claim 6, wherein the outer diameter of the floating ring is no greater than an outer diameter of the annular surface of the flange ring.

\* \* \* \* \*